United States Patent
Filip

(10) Patent No.: US 11,230,680 B2
(45) Date of Patent: Jan. 25, 2022

(54) METHODS FOR PREPARING FUEL ADDITIVES

(71) Applicant: BP OIL INTERNATIONAL LIMITED, Middlesex (GB)

(72) Inventor: Sorin Vasile Filip, Reading (GB)

(73) Assignee: BP OIL INTERNATIONAL LIMITED, Sunbury on Thames (GB)

( * ) Notice: Subject to any disclaimer, the term of this patent is extended or adjusted under 35 U.S.C. 154(b) by 15 days.

(21) Appl. No.: 16/958,730

(22) PCT Filed: Dec. 19, 2018

(86) PCT No.: PCT/EP2018/086022
§ 371 (c)(1),
(2) Date: Jun. 28, 2020

(87) PCT Pub. No.: WO2019/129588
PCT Pub. Date: Jul. 4, 2019

(65) Prior Publication Data
US 2020/0332208 A1    Oct. 22, 2020

(30) Foreign Application Priority Data
Dec. 27, 2017 (GB) .................................... 1721957

(51) Int. Cl.
*C10L 1/233* (2006.01)
*C07D 265/36* (2006.01)
*C10L 1/183* (2006.01)
*C10L 10/10* (2006.01)

(52) U.S. Cl.
CPC ............ *C10L 1/233* (2013.01); *C07D 265/36* (2013.01); *C10L 1/1832* (2013.01); *C10L 10/10* (2013.01); *C10L 2200/0423* (2013.01); *C10L 2270/023* (2013.01); *C10L 2290/24* (2013.01)

(58) Field of Classification Search
CPC ........ C10L 1/233; C10L 1/1832; C10L 10/10; C10L 2200/0423; C10L 2270/023; C10L 2290/24; C07D 265/36
See application file for complete search history.

(56) References Cited

U.S. PATENT DOCUMENTS

| 4,288,589 A | 9/1981 | Loew et al. |
| 4,861,914 A | 8/1989 | Weidig et al. |
| 2005/0261244 A1 | 11/2005 | Tuerdi et al. |
| 2006/0123696 A1 | 6/2006 | Gaughan et al. |
| 2008/0064871 A1 | 3/2008 | Hirata et al. |
| 2009/0094887 A1 | 4/2009 | Calvert et al. |

FOREIGN PATENT DOCUMENTS

| CN | 105272904 A | 4/2019 |
| EP | 2172453 A1 | 4/2010 |
| EP | 3205701 A1 | 8/2017 |
| EP | 3205703 A1 | 8/2017 |

(Continued)

OTHER PUBLICATIONS

Shadyro, O.I. et al. "Synthesis and Antiviral Activity of N-Acyl Derivatives of 4,6-Di-(tert-butyl)-2-aminophenol." Pharmaceutical Chemistry Journal. 2002, 36(8), p. 410-412.
Perry, B. et al. "Achieving multi-isofrom-PI3K inhibition in a series of substituted 3,4-dihydro-2H-benzo[1,4] oxazines." Bioorg Med Chem Lett. 2008, 18, 16, p. 4700-4704.
Dugar, S. et al. "A Concise and Efficient Synthesis of Substituted Morpholines." Synthesis. 2014, 47, 5, p. 712-720.

(Continued)

*Primary Examiner* — Cephia D Toomer
(74) *Attorney, Agent, or Firm* — McDonnell Boehnen Hulbert & Berghoff LLP

(57) ABSTRACT

Methods for preparing an octane-boosting fuel additive having the following formula: are provided. In a first aspect, the method may comprise carrying out the following reaction: (i), (ii) In a second aspect, the method may comprise: (1) preparing the fuel additive; and (2) purifying the product of step (1) by: (a) dissolving the fuel additive in a water-insoluble solvent to form a solution; (b) washing the solution with water; and (c) separating the fuel additive product from the water-insoluble solvent using distillation. Steps (i) and (1) of the methods are carried out in the presence of butylated hydroxytoluene.

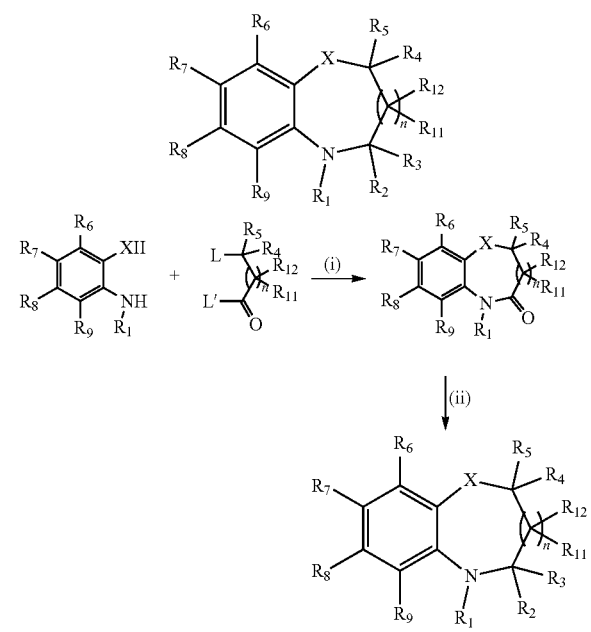

20 Claims, No Drawings

(56) References Cited

FOREIGN PATENT DOCUMENTS

| GB | 1013572 | * | 12/1965 |
|---|---|---|---|
| GB | 2026524 | A | 2/1980 |
| JP | H04247017 | A | 9/1992 |
| KR | 20120102381 | A | 9/2012 |
| WO | 2009001817 | A1 | 12/2008 |
| WO | 2011048112 | A1 | 4/2011 |
| WO | 2011103460 | A1 | 8/2011 |
| WO | 2012009678 | A1 | 1/2012 |
| WO | 2014047390 | A1 | 3/2014 |
| WO | 2015063694 | A1 | 5/2015 |
| WO | 2017108723 | A2 | 6/2017 |
| WO | 2017137518 | A1 | 8/2017 |
| WO | 2017142833 | A1 | 8/2017 |

OTHER PUBLICATIONS

International Search Report and Written Opinion of International Application No. PCT/EP2018/086022, dated Apr. 10, 2019.
Coudert, G. et al. "A new synthesis of 3,4-dihydro-2H-1,4-benzoxazines using solid-liquid phase-transfer catalysis." Synthesis Georg Thieme Verlag. 1979, 7, p. 541-543.
Kotha, S. "Synthesis and Reactions of 3,4-dihydro-2H-1,4-benzoxazine Derivatives." Heterocycles. 1994, 38, p. 5-8.
Hernandez-Olmos, V. et al. "N-Substituted Phenoxazine and Acridone Derivatives: Structure-Activity Relationships of Potent P2X4 Receptor Antagonists." J. Med. Chem. 2012, 55, 22, p. 9576-9588.
Bunce, R.A. et al. "Tetrahydro-1,5-benzoxazepines and tetrahydro-1H-1,5-benzodiazepines by a tandem reduction-reductive amination reaction." J. Heterocyclic Chem. 2004, 41, 6, p. 963-970.
Shadyro, O.I. et al. "Synthesis and Antiviral Activity of N-Acyl Derivatives of 4,6-Di-(tert-butyl)-2-aminophenol." Pharmaceutical Chemistry Journal. 2003, 37, p. 399-401.
International Search Report and Written Opinion for International Application No. PCT/EP2018/086023, dated Jul. 4, 2019.
International Search Report and Written Opinion for International Application No. PCT/EP2018/086027, dated May 10, 2019.
Filippou, P.S. et al. "Regulation of the *Escherichia coli* AtoSC two component system by synthetic biologically active 5;7;8-trimethyl-1;4-benzoxazine analogues." Bioorgan Med Chem. 2011, 19, 16, p. 5061-5070.
Ramesh, C. et al. "A simple and facile route for the synthesis of 2H-1,4-benzoxazin-3-(4H)-ones via reductive cyclization of 2-(2-nitrophenoxy)acetonitrile adducts in the presence of Fe/acetic acid." Tetrahedron. 2011, 67, 6, p. 1187-1192.
Reddy, Ch. R. et al. "Reductive N-alkylation of aromatic amines and nitro compounds with nitriles using polymethylhydrosiloxane." Tetrahedron Let. 2007, 48, 15, p. 2765-2768.
International Search Report and Written Opinion for International Application No. PCT/EP2018/086025, dated Jun. 6, 2019.
Bartsch, H. et al. "Synthese und Reaktivität von 2- und 3-hydroxylierten Dihydro-1,4-Benzoxazinen." Monatshefte für Chemie. 1997, 110, p. 267-278.
Mizar, P. et al. "Synthesis of substituted 4-(3-alkyl-1,2,4-oxadiazol-5-ylmethyl)-3,4-dihydro-2H-1,4-benzoxazines and 4-(1H-benzimidazol-2-ylmethyl)-3,4-dihydro-2H-1,4-benzoxazines." Tetrahedron Let. 2006, 47, 44, p. 7823-7826.
Fu, Y. et al. "Simple and efficient synthesis of novel N-dichloroacetyl-3,4-dihydro-2H-1,4-benzoxazines." Heterocycl Commun. 2012, 18, 3, p. 143-146.
International Search Report and Written Opinion for International Application No. PCT/EP2018/086024, dated Jun. 6, 2019.
Knorr, L. "Synthesen in der »Oxazinreihe«." Ber. Dtsch. Chem. Ges. 1889, 22, p. 2081-2099.
Calderone, V. et al "Structural modifications of benzanilide derivatives, effictive potassium channel openers. X." Eur. J. Med. Chem. 2006, 41(12), p. 1421-1429.
Liu, Y. et al. "Concise synthesis of 3,4-dihydro-1,4-benzoxazines by three-component reactions of acyl chlorides, o-aminophenols and 1,2-dichloroethane." Tetrahedron. 2018, 74(27), p. 3691-3696.
Huerta, G. et al. "Facile Synthesis of Aminoalcohols by Ring Opening of Epoxides Under Solvent Free Conditions." Synthetic Commun. 2004, 34(13), p. 2393-2406.
Woydowski, K. "Optically Active Heterocycles through Ring Transformations on Oxirane3-carboxylate Derivatives." Sel. Org. React. Database (SORD). 1999. See CASREACT abstract accession No. 161:698073.
Gao, S. et al. "Synthesis and crystal structure of N-dichloroacetyl-3,4-dihydro-3-methyl-6-chloro-2H-1,4-benzoxazine". Journal of Chemistry. 2015, 2015, Article ID 268306, p. 1-5.
Yang, J. et al. "Synthesis, anti-cancer evaluation of benzenesulfoamide derivates as potent tubulin-targeting agents." Eur. J. Med. Chem. 2016, 122, p. 488-496.

* cited by examiner

METHODS FOR PREPARING FUEL ADDITIVES

This application is a national stage application under 35 U.S.C. § 371 of International Application No. PCT/EP2018/086022, filed Dec. 19, 2018, which claims priority to Great Britain Application No. 1721957.7, filed Dec. 27, 2017, the disclosures of which are explicitly incorporated by reference herein.

FIELD OF THE INVENTION

This invention relates to methods for preparing octane-boosting additives for use in a fuel for a spark-ignition internal combustion engine. In particular, the invention relates to methods for preparing octane-boosting fuel additives that are derivatives of benzo[1,4]oxazines and 1,5-benzoxazepines. The invention further relates to methods for preparing fuels for a spark-ignition internal combustion engine comprising the fuel additives.

BACKGROUND OF THE INVENTION

Spark-ignition internal combustion engines are widely used for power, both domestically and in industry. For instance, spark-ignition internal combustion engines are commonly used to power vehicles, such as passenger cars, in the automotive industry.

Fuels for a spark-ignition internal combustion engine (generally gasoline fuels) typically contain a number of additives to improve the properties of the fuel.

One class of fuel additives is octane-improving additives. These additives increase the octane number of the fuel which is desirable for combatting problems associated with pre-ignition, such as knocking. Additisation of a fuel with an octane improver may be carried out by refineries or other suppliers, e.g. fuel terminals or bulk fuel blenders, so that the fuel meets applicable fuel specifications when the base fuel octane number is otherwise too low.

Organometallic compounds, comprising e.g. iron, lead or manganese, are well-known octane improvers, with tetraethyl lead (TEL) having been extensively used as a highly effective octane improver. However, TEL and other organometallic compounds are generally now only used in fuels in small amounts, if at all, as they can be toxic, damaging to the engine and damaging to the environment.

Octane improvers which are not based on metals include oxygenates (e.g. ethers and alcohols) and aromatic amines. However, these additives also suffer from various drawbacks. For instance, N-methyl aniline (NMA), an aromatic amine, must be used at a relatively high treat rate (1.5 to 2% weight additive/weight base fuel) to have a significant effect on the octane number of the fuel. NMA can also be toxic. Oxygenates give a reduction in energy density in the fuel and, as with NMA, have to be added at high treat rates, potentially causing compatibility problems with fuel storage, fuel lines, seals and other engine components.

Any additive that is included in a fuel must be provided in a form which does not take the fuel off specification. For instance, gasoline specifications, e.g. EN 228, will generally require the fuel to be classified as 'clear and bright' (or similar) by visual inspection, but some additives can contribute to the discoloration of a fuel. Many gasoline fuel specifications also restrict the sulfur content and the phosphorus content of a fuel, and limits are also typically placed on the metals content permitted in a fuel. Where an additive product is not provided in a pure form, it can contribute to the loading of these components in a fuel.

A fuel additive must also be provided in a form that is stable. Whilst some fuel additives are stable and do not require the addition of any further stabilising components, others do require stabilisation. In these cases, stabilising additives are typically blended into at least one of the additive composition and fuel itself. The addition of these stabilising additives can be costly and increase the complexity of the blending process.

Recently, a new class of octane-boosting additive has been discovered. These octane-boosting additives are derivatives of benzo[1,4]oxazines and 1,5-benzoxazepines, and show great promise due to their non-metallic nature, their low oxygenate content, and their octane-boosting performance at low treat rates (see WO 2017/137518). Other advantages are also associated with the new class of octane-boosting additives, including their efficacy as anti-oxidants.

Synthesis routes currently reported in the literature provide various descriptions of how benzoxazines may be prepared on a relatively small scale (hundreds of mg to up to 100 kg scale). For example, US 2008/064871—which relates to compounds for the treatment or prophylaxis of diseases relating to uric acid, such as gout—discloses the preparation of benzoxazine-derived compounds. However, there is a need for a method which is suitable for the production of the new class of octane-boosting additives on an industrial scale, e.g. in an amount of from 50 to 20,000 tonnes per year.

Butylated hydroxytoluene (also known as BHT, dibutylhydroxytoluene and 2,6-di-tert-butyl-4-methylphenol) is known as an anti-oxidant. For instance, U.S. Pat. No. 4,861,914 discloses the use of BHT for stabilising alkylated aromatic amines used as intermediates in the preparation of polymers. BHT is also known for preventing the polymerisation of hydrocarbons in fuels for a spark-ignition internal combustion engine. However, it has not previous been used for stabilising fuel additives.

Accordingly, there is a need for methods for synthesising the new class of octane-boosting additives which mitigate at least some of the problems highlighted above, e.g. by providing the additives in a form which is desirable in a fuel and, preferably, on a large scale.

SUMMARY OF THE INVENTION

Surprisingly, it has now been found that, by preparing a fuel additive e having the formula:

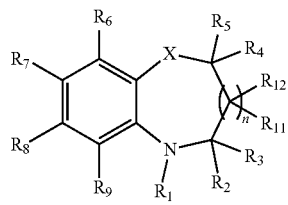

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;

X is selected from —O— or —NR$_{10}$—, where R$_{10}$ is selected from hydrogen and alkyl groups; and n is 0 or 1, in the presence of butylated hydroxytoluene (BHT), the fuel additive e may be provided in a form which is resistant to degradation, even after purification.

Without wishing to be bound by theory, it is believed that BHT is highly soluble in the fuel additive e, and therefore remains entrained in fuel additive e throughout processing. The entrained BHT stabilises the fuel additive e, even at very low treat rates. Since fuel additive e is itself effective as an anti-oxidant, it is surprising that BHT has this effect.

Accordingly, in a first aspect, the present invention provides a method for preparing a fuel additive e, said method comprising carrying out the following reaction:

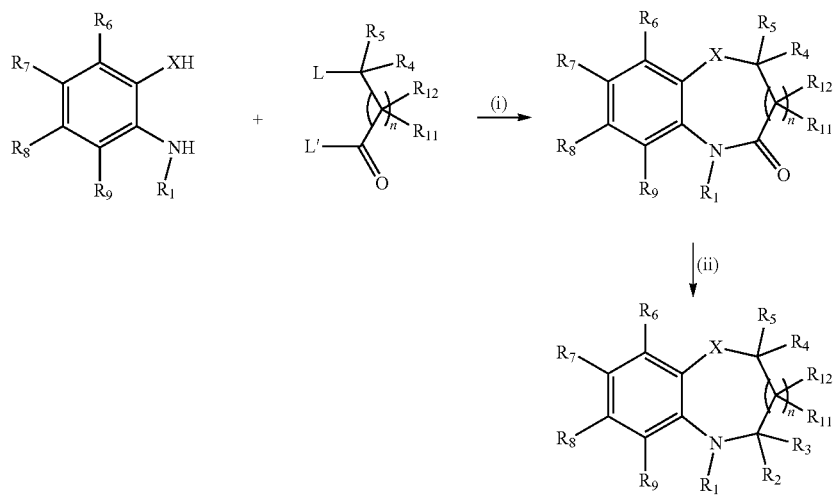

where: L and L' are each independently selected from leaving groups, wherein step (i) is carried out in the presence of BHT.

In a second aspect, the present invention further provides a method for preparing a fuel additive e, said method comprising the following steps:

(1) preparing the fuel additive in the presence of BHT; and
(2) purifying the fuel additive by: (a) dissolving the fuel additive in a water-insoluble solvent to form a solution; (b) washing the solution with water; and (c) separating the fuel additive product from the water-insoluble solvent using distillation.

Also provided is an additive composition for a fuel for a spark-ignition internal combustion engine, said additive composition comprising:

a fuel additive e; and

BHT.

The present invention further provides a process for preparing a fuel composition for a spark-ignition internal combustion engine, said process comprising blending an additive composition of the present invention with a base fuel. A fuel composition for a spark-ignition internal combustion engine which comprises an additive composition of the present invention and a base fuel is also provided.

Further provided is the use of BHT for stabilising a fuel additive e, as well as a method for stabilising a fuel additive e in which the fuel additive is blended with BHT.

DETAILED DESCRIPTION OF THE INVENTION

Preparation Methods

The present invention provides a method for preparing a fuel additive e.

In a first aspect, the method comprises carrying out the following reaction:

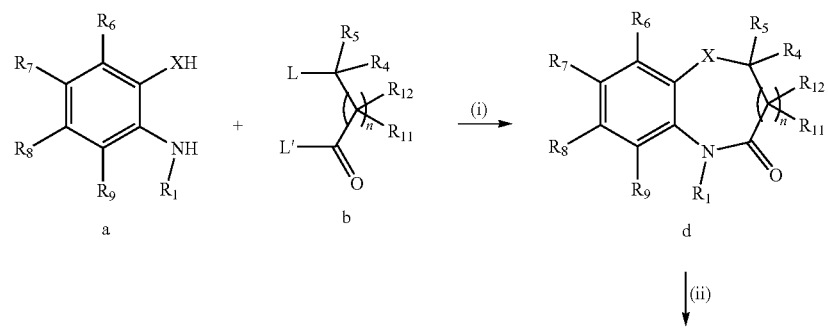

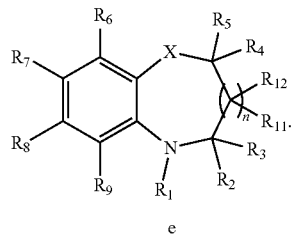

e

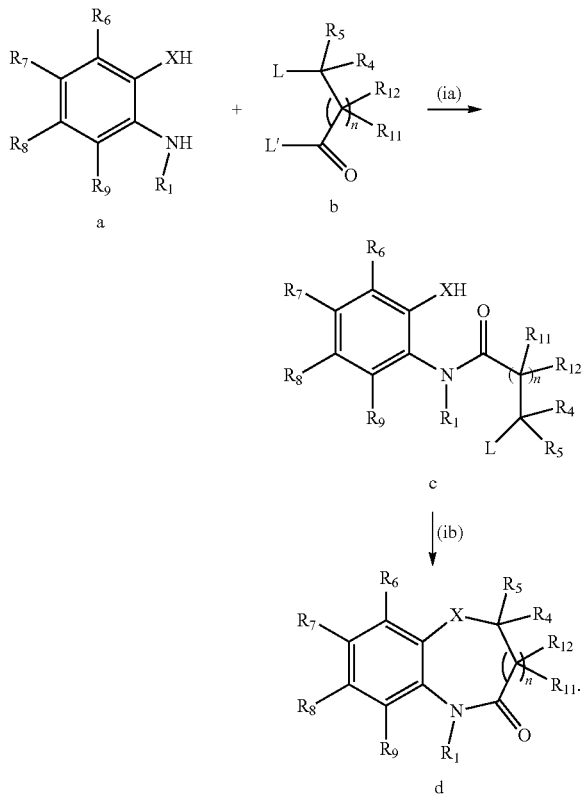

Reagent b may be used in an amount of from 0.8 to 2 molar equivalents, preferably from 0.9 to 1.5 molar equivalents, and more preferably from 1 to 1.2 molar equivalents as compared to starting material a.

In some embodiments, step (i) is carried out as a single reaction (i.e. with one set of reagents and under one set of conditions). However, in other embodiments, step (i) comprises the following sub-steps:

It will be appreciated that, in some instances, step (ib) will occur spontaneously on formation of intermediate c. For the purposes of the present invention, these instances are considered to be embodiments in which step (i) is carried out as a single reaction.

Where step (i) comprises sub-steps (ia) and (ib), either or both of these steps may be carried out in the presence of BHT. Preferably at least sub-step (ia) is carried out in the presence of BHT.

Step (ia) involves the addition of reagent b to starting material a to form intermediate c.

Step (ia) is preferably conducted in the presence of a base, such as an inorganic base. Preferred bases are selected from alkali metal carbonates, such as sodium bicarbonate, sodium carbonate, potassium bicarbonate and potassium carbonate. Sodium bicarbonate is particularly suited for carrying out step (ia).

The base may be used in an amount of from 0.7 to 2 molar equivalents, preferably from 0.8 to 1.5 molar equivalents, and more preferably from 1 to 1.25 molar equivalents as compared to starting material a.

Step (ia) is preferably conducted in the presence of an aprotic solvent. Aprotic solvents are well-known in the art as solvents which are not capable of donating protons. Aprotic solvents do not contain hydrogen atoms directly bound to a nitrogen or an oxygen.

Preferred aprotic solvents for carrying out step (ia) are selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butyl formate, ethyl acetate, isobutyronitrile, methyl acetate, methyl formate, nitromethane, oxolane and propionitrile, and more preferably from tetrahydrofuran, acetonitrile, dimethoxyethane and dioxane, with tetrahydrofuran particularly preferred.

The aprotic solvent may be used in an amount of from 5 to 20 equivalents, preferably from 8 to 17 equivalents, and more preferably from 10 to 15 equivalents by volume relative to starting material a.

The reaction mixture is preferably cooled during step (ia), e.g. to a temperature of up to 18° C., such as to a temperature of from 0 to 18° C., preferably to a temperature of from 3 to 15° C., and more preferably to a temperature of from 5 to 10° C. Cooling may be carried out by known means, e.g. a cooling bath.

Step (ia) is preferably conducted at ambient pressure, i.e. a pressure of approximately 1 bar.

The reaction in step (ia) is preferably conducted for at least 2 hours, preferably at least 4 hours and more preferably at least 5 hours. During this period, reagent b is preferably added to starting material a dropwise, for instance over at least the first 2 hours, preferably at least the first 3 hours, and more preferably at least the first 4 hours of the reaction time.

In a very specific embodiment, step (ia) is carried out in the presence of a base (e.g. sodium bicarbonate), a solvent (e.g. tetrahydrofuran), and at a temperature of 5 to 10° C.

In step (ib), intermediate c is subjected to a ring-closing reaction.

As with step (ia), step (ib) is also preferably conducted in the presence of a base.

The base may be used in step (ib) in an amount of from 0.7 to 2 molar equivalents, preferably from 0.8 to 1.5 molar equivalents, and more preferably from 1 to 1.25 molar equivalents as compared to intermediate c.

The base is preferably selected from inorganic bases, and more preferably from alkali metal carbonates, such as sodium bicarbonate, sodium carbonate, potassium bicarbonate and potassium carbonate.

An aprotic solvent is preferably used with the inorganic bases in step (ib). The aprotic solvent is preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butyl formate, ethyl acetate, isobutyronitrile, methyl acetate, methyl formate, nitromethane, oxolane and propionitrile, and more preferably from tetrahydrofuran, acetonitrile, dimethoxyethane and dioxane. Tetrahydrofuran is more preferably used.

The aprotic solvent may be used in step (ib) an amount of from 5 to 20 equivalents, preferably from 8 to 17 equivalents, and more preferably from 12 to 18 equivalents by volume relative to starting material a. At least some, e.g. at least 75%, of the aprotic solvent may be introduced into the reaction vessel used for step (ib) as part of a reaction mixture containing intermediate c from step (ia).

Chlorinated solvents, such as chloroform or dichloroethane, may also be used with inorganic bases. In these instances, a phase-transfer reagent is also preferably used. Suitable phase-transfer agents include quaternary ammonium salts such as tetraalkylammonium halide salts, e.g. butyltriethylammonium chloride.

The base may also be selected from organic bases. For instance, the base may be selected from nitrogen-containing organic bases, preferably from triethylamine, diisopropylethylamine and 1,8-diazabicyclo[5.4.0]undec-7-ene.

An aprotic solvent, preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butyl formate, ethyl acetate, isobutyronitrile, methyl acetate, methyl formate, nitromethane; oxolane and propionitrile and more preferably from dimethylformamide, N-methyl-2-pyrrolidone, dimethyl sulfoxide and sulfolane, is preferably used with organic bases in step (ib).

The reaction mixture is preferably heated during step (ib), e.g. to a temperature of at least 40° C., such as to a temperature of from 40 to 80° C., preferably to a temperature of from 55 to 70° C., and more preferably to a temperature of from 60 to 65° C.

Step (ib) is preferably conducted at ambient pressure, i.e. a pressure of approximately 1 bar.

The reaction in step (ib) is preferably conducted for at least 2 hours, preferably at least 5 hours and more preferably at least 10 hours.

In a very specific embodiment, step (ib) is carried out in the presence of a base (e.g. potassium carbonate), a solvent (e.g. tetrahydrofuran), and at a temperature of 60 to 65° C.

During step (i), the leaving groups L and L' are lost from reagent b.

Leaving group L is preferably selected from: halides (e.g. Cl, Br, I), substituted aryloxy groups (e.g. —O—Ar, where Ar is selected from nitro-substituted aryl groups such as p-nitrophenyl) and sulfonates (e.g. —OSO$_2$A, where A is selected from tolyl, methyl, —CF$_3$, —CH$_2$Cl, phenyl and p-nitrophenyl). More preferably, leaving group L is selected from halides, and even more preferably from Cl and Br.

Leaving group L' is preferably selected from: halides (e.g. Cl, Br, I) and alkoxy groups (e.g. —OMe and —OEt). More preferably, leaving group L' is selected from halides, and even more preferably from Cl and Br.

Step (ii) of the method involves the conversion of intermediate d to the target fuel additive e:

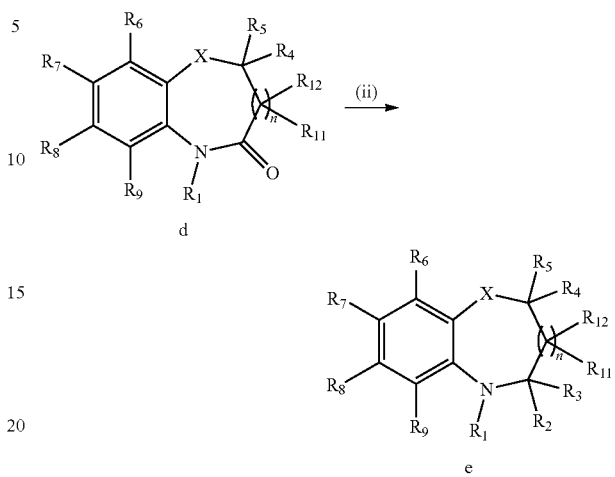

Step (ii) of the method may be carried out in the presence of a reducing agent or using catalytic reduction.

Where step (ii) is carried out in the presence of a reducing agent, preferred reducing agents are selected from sodium bis(2-methoxyethoxy)aluminumhydride (known as 'Red-Al'), lithium aluminium hydride, borane (preferably in combination with dimethyl sulfide), diisobutylaluminium hydride, and borohydrides. Suitable borohydrides include: sodium borohydride, preferably in combination with boron trifluoride diethyl etherate, iodine, titanium tetrachloride, cobalt (II) chloride or acetic acid; lithium borohydride, preferably in combination with trimethylsilyl chloride; and zinc borohydride.

Where Red-Al is used, this is preferably in combination with an alkali metal halide, such as potassium fluoride. The alkali metal halide may be used in an amount of from 0.1 to 1%, preferably from 0.2 to 0.6% by weight of intermediate d.

The reducing agent may be added dropwise to the reaction mixture, e.g. over a period of at least 2 hours, preferably at least 3 hours, and more preferably at least 4 hours.

The reducing agent may be used in sub-step (ii) in an amount of from 1 to 4 molar equivalents, preferably from 1.5 to 3 molar equivalents, and more preferably from 1.75 to 2.25 molar equivalents, as compared to intermediate d.

An aprotic solvent is preferably used with the reducing agent, for instance an aprotic solvent selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butyl formate, ethyl acetate, isobutyronitrile, methyl acetate, methyl formate, nitromethane, oxolane and propionitrile and more preferably from toluene, tetrahydrofuran, dimethoxyethane and dioxane. In some embodiments, tetrahydrofuran is preferred for use as the aprotic solvent The aprotic solvent may be used in step (ii) an amount of from 4 to 20 equivalents, preferably from 6 to 16 equivalents, and more preferably from 8 to 12 equivalents by weight relative to intermediate d.

Preferred combinations of reducing agent/solvent are as follows:
Red-Al/toluene
lithium aluminium hydride/tetrahydrofuran or dimethoxyethane or dioxane borane, in combination with dimethyl sulfide/tetrahydrofuran diisobutylaluminium hydride/tetrahydrofuran sodium borohydride, boron trifluoride diethyl etherate/tetrahydrofuran sodium borohydride, iodine/tetrahydrofuran lithium borohydride, trimethylsilyl chloride/tetrahydrofuran sodium borohydride, titanium tetrachloride/dimethoxyethane zinc borohydride/tetrahydrofuran sodium borohydride, cobalt (II) chloride/tetrahydrofuran sodium borohydride, acetic acid/dioxane Where step (ii) is carried out in the presence of a reducing agent, it is preferably carried out at ambient temperature (i.e. at a temperature of from 15 to 25° C.). Since the reaction may be exothermic, the reaction mixture may require cooling to maintain the temperature in this range. In other embodiments, the reaction may be cooled e.g. to a temperature of lower than 15° C., such as from 0 to 10° C.

The reaction is preferably carried out at ambient pressure, i.e. a pressure of approximately 1 bar.

Where step (ii) is carried out in the presence of a reducing agent, the reaction may be quenched using a base, preferably an inorganic base such as an alkali metal hydroxide. Sodium hydroxide and potassium hydroxide are preferred, particularly sodium hydroxide.

The base that is used for quenching may be added dropwise over a period of at least 30 minutes, preferably at least 1 hour, and more preferably at least 2 hours.

Where step (ii) is carried out using catalytic reduction, it may be carried out in the presence of hydrogen at a pressure of from 1 to 80 bar, preferably from 3 to 60 bar, and more preferably from 5 to 50 bar.

Suitable catalysts include ruthenium, platinum, palladium and rhodium catalysts, with ruthenium catalysts such as ruthenium (III) acetylacetonate preferred. Other metal catalysts may also be used, such as those containing a mixture of copper and chromium (e.g. copper chromite). Mixtures of copper and chromium are preferably used in combination with a zeolite molecular sieve (e.g. having a pore size of approximately 4 Å). Iridium catalysts may also be used. In some embodiments, iridium and rhodium catalysts are used in the presence of a silane. Suitable silanes include alkyl silanes such as diethylsilane.

In some particularly preferred embodiments, a ruthenium hydrogenation catalyst may be formed in-situ in step (ii) from a mixture of ruthenium (III) acetylacetonate and a triphos (e.g. 1,1,1-tris(diphenylphosphinomethyl)ethane) and optionally also: ytterbium (III) trifluoromethanesulfonate, preferably in the presence of methanesulfonic acid and trifluoromethanesulfonimide; or methane sulfonic acid.

Where step (ii) is carried out using catalytic reduction, an aprotic solvent is preferably used with the catalyst. The aprotic solvent may be selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butyl formate, ethyl acetate, isobutyronitrile, methyl acetate, methyl formate, nitromethane, oxolane and propionitrile and is preferably tetrahydrofuran.

In some embodiments, step (ii) is carried out in the presence of BHT, for example which has been introduced as part of the solvent system in which the reaction is conducted. In some embodiments, BHT is not used in the method for preparing the fuel additive other than as part of the solvent system in which step (i) and optionally step (ii) is conducted.

Where step (ii) is carried out using catalytic reduction, the reaction may be conducted at a temperature of greater than 80° C., preferably greater than 100° C., and more preferably greater than 120° C.

The reaction in step (ii) is preferably conducted for at least 2 hours, preferably at least 5 hours and more preferably at least 10 hours.

In a very specific embodiment, step (ii) is carried out in the presence of a reducing agent (e.g. Red-Al), a solvent (e.g. toluene), and at a temperature of 10 to 20° C. The reaction is quenched using a base (e.g. sodium hydroxide).

In another very specific embodiment, step (ii) is carried out in the presence of a reducing agent (e.g. lithium aluminium hydride), a solvent (e.g. tetrahydrofuran) with the temperature maintained at below 10° C.

In another very specific embodiment, step (ii) is carried out in the presence of a reducing agent (e.g. borane), a solvent (e.g. tetrahydrofuran) and at a temperature of 0 to 5° C.

In other embodiments, where step (ii) is carried out using catalytic reduction, it may be carried out in the absence of hydrogen gas, e.g. hydrogen gas is present at a level of less than 10 ppm and preferably less than 1 ppm by volume. In these embodiments, the reaction is carried out in the presence of a silane hydrogen source. Suitable silanes include alkoxy silanes (e.g. $(EtO)_3SiH$) and aryl silanes (e.g. $PhSiH_3$).

Preferred catalysts for carrying out the reaction in the absence of hydrogen gas are selected from metal catalysts. Preferably the catalyst is selected from ruthenium and zinc catalysts. The catalyst may be used in an amount of up to 0.5 molar equivalents, preferably from 0.01 to 0.15 molar equivalents as compared to intermediate d.

Where step (ii) is carried out using catalytic reduction but in the absence of hydrogen gas, step (ii) is preferably conducted in the presence of a solvent, preferably selected from aprotic solvents such as those listed previously in connection with step (ii), and is preferably tetrahydrofuran.

Where step (ii) is carried out using catalytic reduction but in the absence of hydrogen gas, step (ii) may be conducted at a temperature of greater than 10° C., preferably from 15 to 50° C., and more preferably from 20 to 40° C.

Where step (ii) is carried out using catalytic reduction but in the absence of hydrogen gas, step (ii) may be conducted at ambient pressure, i.e. approximately 1 bar. The reaction may be carried out under an inert atmosphere, e.g. an under argon.

Where step (ii) is carried out using catalytic reduction but in the absence of hydrogen gas, the reaction may be conducted for a period of greater than 20 minutes, preferably greater than 1 hour, but preferably less than 24 hours.

In preferred embodiments, the method of the present invention further comprises a step of purifying the fuel additive to give a purified fuel additive product. This step reduces the level of impurities that may be present in the crude fuel additive product, such as unreacted reagents and by-products. In particular, the purification may be used to remove the following dimer by-product which, without wishing to be bound by theory, is believed to form during step (ii):

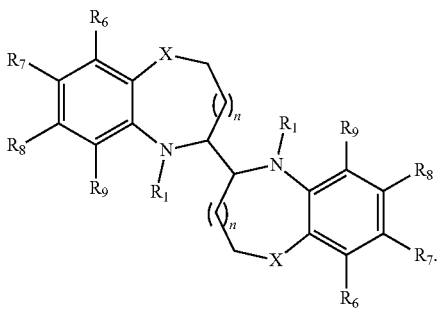

This dimer by-product is pink in colour and, if not removed, may contribute to the discoloration of a fuel in which it is used. For simplicity, the dimer by-product has been shown with $R_2$, $R_4$, $R_5$, $R_{11}$ and $R_{12}$ all being H.

The step of purifying fuel additive e preferably comprises: (a) dissolving the fuel additive in a water-insoluble solvent to form a solution; (b) washing the solution with water; and (c) separating the fuel additive product from the water-insoluble solvent using distillation.

In a second aspect, the present invention provides a method for preparing fuel additive e which comprises the following steps:
(1) preparing the fuel additive in the presence of BHT; and
(2) purifying the fuel additive by: (a) dissolving the fuel additive in a water-insoluble solvent to form a solution; (b) washing the solution with water; and (c) separating the fuel additive product from the water-insoluble solvent using distillation.

It will be appreciated that step (1) may be carried out using methods described herein, or by using any other method.

The following passages, relating to purification of the fuel additive, apply to both the first and second aspects of the present invention.

In step (a) of the purification method, the fuel additive is dissolved in a water-insoluble solvent. The water-insoluble solvent is preferably toluene.

The fuel additive and water-insoluble solvent may be agitated, e.g. by stirring. Agitation may improve (e.g. speed up) dissolution of the fuel additive.

In step (b), the solution formed in step (a) is washed with water. It will be appreciated that step (b) comprises: (bi) adding water to the solution (i.e. the water-insoluble solvent in which the fuel additive is dissolved), and (bii) separating the non-aqueous phase from the aqueous phase.

Preferably, the mixture of water and water-insoluble solvent are mixed, e.g. by reflux, before they are separated. This enhances transfer of impurities between the aqueous and non-aqueous phases.

In some instances, the solution may be washed in step (b) more than once with water, for instance, twice or preferably three times.

In some instances, the aqueous phase, or each of the separated aqueous phases, separated in step (bii) is washed with further water-insoluble solvent. This further water-insoluble solvent may then be combined with the water-insoluble solvent in which the fuel additive is dissolved from step (bii) before separation of the fuel additive product in step (c).

Any conventional distillation technique can be used for step (c), e.g. fractional distillation. Where purification involves distillation into fractions, each of the fractions comprising fuel additive e is preferably combined to form the purified fuel additive product.

Where toluene is used as the water-insoluble solvent, the toluene is removed by distillation first, followed by the fuel additive e with BHT entrained therein. Any dimer by-product will typically be retained in the distillation residue.

Suitable conditions for distillation include a starting temperature of about 60° C. and a vacuum of about 200 mbar. The temperature may then be increased and the pressure reduced until reflux and then distillation are achieved.

The purified fuel additive product contains fuel additive e in an amount of greater than 97%, preferably greater than 98%, and more preferably greater than 99% by weight of the product. The % by weight of fuel additive e in the purified fuel additive product may be measured using HPLC, with the ratio of fuel additive e peak area to total peak area assumed to equal the ratio by weight. HPLC may be carried out using the conditions detailed in the Examples. Sample preparation may also be carried out as detailed in the Examples.

The purified fuel additive product preferably contains aluminium in an amount of less than 100 ppm, and more preferably less than 50 ppm.

The purified fuel additive product preferably contains potassium in an amount of less than 100 ppm, and more preferably less than 50 ppm.

The purified fuel additive product preferably contains sodium in an amount of less than 100 ppm, and more preferably less than 50 ppm.

The content of aluminium, potassium and sodium in the purified fuel additive product may be measured according to ASTM D7111-16.

The purified fuel additive product preferably contains chlorine in an amount of less than 100 ppm, and more preferably less than 50 ppm. The chlorine content may be measuring using inductively coupled plasma atomic emission spectrometry.

The purified fuel additive product preferably contains sulfur in an amount of less than 100 ppm, and more preferably less than 50 ppm. The sulfur content of the purified fuel additive product may be measured according to EN ISO 20846:2011.

The present invention is based on the discovery that the BHT that is present in step (i) or step (1) of the methods of the present invention remains entrained in the fuel additive e throughout processing, including purification, and is effective at stabilising the fuel additive e. Thus, the methods of the present invention are used to prepare the fuel additive e in a form in which BHT is entrained.

In some embodiments, the methods comprise preparing the fuel additive e in a form which contains BHT in an amount of from 0.01 to 1.5%, preferably from 0.05 to 1.0%, and more preferably from 0.1 to 0.8% by weight of the fuel additive e. The % of BHT by weight of fuel additive e may be measured using HPLC, with the ratio of BHT peak area to fuel additive e peak area assumed to equal the ratio by weight. HPLC may be carried out using the conditions detailed in the Examples. Sample preparation may also be carried out as detailed in the Examples. Since BHT remains entrained in the fuel additive e throughout processing, it will be appreciated that these amounts apply to a fuel additive product in its unpurified form, as well as once purified.

In preferred embodiments, BHT is introduced as part of the solvent system in which the reaction is conducted. For instance, tetrahydrofuran is preferably used as a solvent in steps (i) and (1), and BHT may be present in the tetrahydrofuran in an amount of from 50 to 1000 ppm, preferably from 100 to 500 ppm and more preferably from 200 to 400 ppm, by weight.

In some embodiments, more than 30%, preferably more than 40%, and more preferably more than 50% by weight of the BHT that is used in steps (i) and (1) remains entrained in the fuel additive e throughout processing. It will be appreciated that this is the case even when the fuel additive is purified.

The method of the present invention is preferably carried out on an industrial scale. For instance, where the method is a batch process, the fuel additive e is preferably produced in a batch quantity of greater than 100 kg, preferably greater than 150 kg, and more preferably greater than 200 kg. The method may also be carried out as a continuous process.

In order to produce the fuel additive e on an industrial scale, steps (i), (ii) and (1) are preferably carried out in reactors having a capacity of at least 500 L, preferably at least 750 L, and more preferably at least 1000 L. It will be appreciated that, where the reaction comprises steps, more than one (e.g. each) step may be carried out in the same reactor.

Octane-Boosting Fuel Additive e

Fuel additives e that are prepared using the methods of the present invention have the following formula:

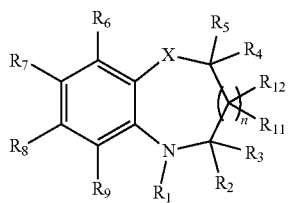

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1.

Preferred substituents for the fuel additives are described below. It will be appreciated that the preferred substitution patterns also apply to the starting material a, reagent b and intermediates c and d from which a fuel additive e is prepared.

In some embodiments, $R_4$, $R_5$, $R_{11}$ and $R_{12}$ are each independently selected from hydrogen and alkyl groups, and preferably from hydrogen, methyl, ethyl, propyl and butyl groups. More preferably, $R_4$, $R_5$, $R_{11}$ and $R_{12}$ are each independently selected from hydrogen, methyl and ethyl, and even more preferably from hydrogen and methyl.

In some embodiments, $R_6$, $R_7$, $R_8$ and $R_9$ are each independently selected from hydrogen, alkyl and alkoxy groups, and preferably from hydrogen, methyl, ethyl, propyl, butyl, methoxy, ethoxy and propoxy groups. More preferably, $R_6$, $R_7$, $R_8$ and $R_9$ are each independently selected from hydrogen, methyl, ethyl and methoxy, and even more preferably from hydrogen, methyl and methoxy.

Advantageously, at least one of $R_4$, $R_5$, $R_6$, $R_7$, $R_8$, $R_9$, $R_{11}$ and $R_{12}$, and preferably at least one of $R_6$, $R_7$, $R_8$ and $R_9$, is selected from a group other than hydrogen. More preferably, at least one of $R_7$ and $R_8$ is selected from a group other than hydrogen. Alternatively stated, the octane-boosting fuel additive may be substituted in at least one of the positions represented by $R_4$, $R_5$, $R_6$, $R_7$, $R_8$, $R_9$, $R_{11}$ and $R_{12}$, preferably in at least one of the positions represented by $R_6$, $R_7$, $R_8$ and $R_9$, and more preferably in at least one of the positions represented by $R_7$ and $R_8$. It is believed that the presence of at least one group other than hydrogen may improve the solubility of the fuel additives e in a fuel.

Also advantageously, no more than five, preferably no more than three, and more preferably no more than two, of $R_4$, $R_5$, $R_6$, $R_7$, $R_8$, $R_9$, $R_{11}$ and $R_{12}$ are selected from a group other than hydrogen. Preferably, one or two of $R_4$, $R_5$, $R_6$, $R_7$, $R_8$, $R_9$, $R_{11}$ and $R_{12}$ are selected from a group other than hydrogen. In some embodiments, only one of $R_4$, $R_5$, $R_6$, $R_7$, $R_8$, $R_9$, $R_{11}$ and $R_{12}$ is selected from a group other than hydrogen.

In preferred embodiments, at least one of $R_4$, $R_5$, $R_7$ and $R_8$ is selected from methyl, ethyl, propyl and butyl groups and the remainder of $R_4$, $R_5$, $R_6$, $R_7$, $R_8$, $R_9$, $R_{11}$ and $R_{12}$ are hydrogen. More preferably, at least one of $R_7$ and $R_8$ are selected from methyl, ethyl, propyl and butyl groups and the remainder of $R_4$, $R_5$, $R_6$, $R_7$, $R_8$, $R_9$, $R_{11}$ and $R_{12}$ are hydrogen.

In further preferred embodiments, at least one of $R_4$, $R_5$, $R_7$ and $R_8$ is a methyl group and the remainder of $R_4$, $R_5$, $R_6$, $R_7$, $R_8$, $R_9$, $R_{11}$ and $R_{12}$ are hydrogen. More preferably, at least one of $R_7$ and $R_8$ is a methyl group and the remainder of $R_4$, $R_5$, $R_6$, $R_7$, $R_8$, $R_9$, $R_{11}$ and $R_{12}$ are hydrogen.

Preferably, X is —O— or —$NR_{10}$—, where $R_{10}$ is selected from hydrogen, methyl, ethyl, propyl and butyl groups, and preferably from hydrogen, methyl and ethyl groups. More preferably, $R_{10}$ is hydrogen. In preferred embodiments, X is —O—.

n may be 0 or 1, though it is preferred that n is 0.

Octane-boosting fuel additives that may be used in the present invention include:

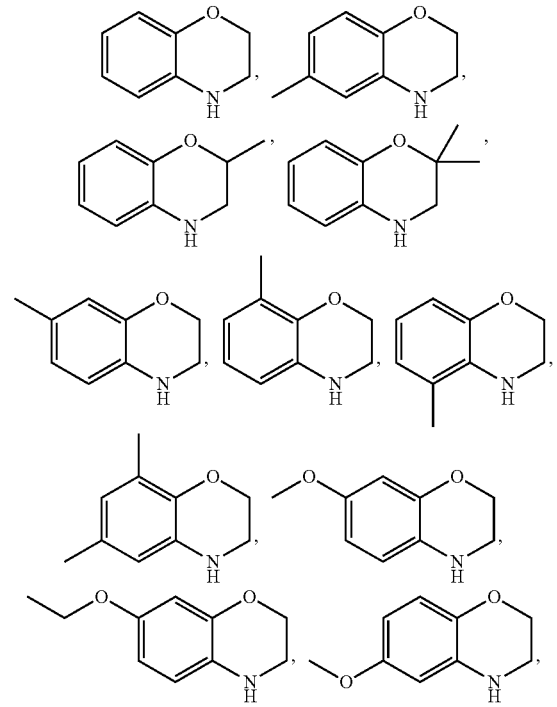

-continued

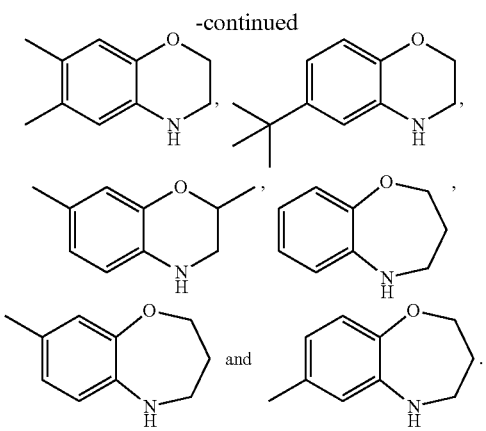

Preferred octane-boosting fuel additives include:

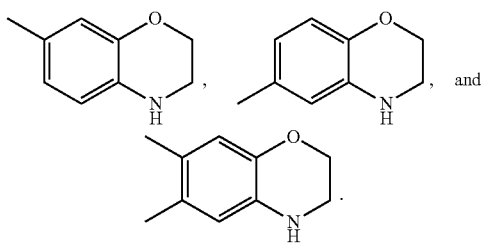

Particularly preferred is the fuel additive:

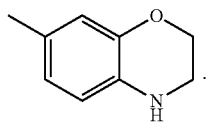

A mixture of fuel additives e may be used in the fuel composition. For instance, the fuel composition may comprise a mixture of:

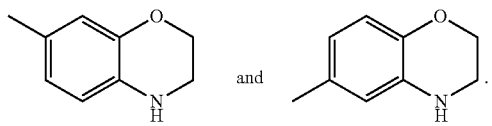

It will be appreciated that references to alkyl groups include different isomers of the alkyl group. For instance, references to propyl groups embrace n-propyl and i-propyl groups, and references to butyl embrace n-butyl, isobutyl, sec-butyl and tert-butyl groups.

Additive Compositions, Fuel Compositions, Uses and Methods

The present invention also provides an additive composition for a fuel for a spark-ignition internal combustion engine, said additive composition comprising:
 a fuel additive e; and
 BHT.

The additive composition preferably comprises BHT in an amount of from 0.01 to 1.5%, preferably from 0.05 to 1.0%, and more preferably from 0.1 to 0.8% by weight of the fuel additive e.

The additive composition preferably comprises fuel additive e in an amount of greater than 97%, preferably greater than 98%, and more preferably greater than 99% of the product.

Methods for measuring the content of BHT and the content of fuel additive e are provided above.

In some embodiments, the additive composition is obtainable using a method of the present invention. Preferably, the additive composition is obtained using a method of the present invention.

The present invention also provides a process for preparing a fuel composition for a spark-ignition internal combustion engine, said process comprising blending an additive composition of the present invention with a base fuel.

The process may further comprise blending additional BHT with the base fuel, preferably to give a total amount of BHT of up to 1000 ppm, more preferably up to 500 ppm, still more preferably up to 100 ppm, and most preferably from 20 to 50 ppm by weight of the base fuel.

The additional BHT may be blended with the base fuel by introduction of the additional BHT into the additive composition of the present invention before it is blended with the base fuel, or by introduction of additional BHT directly into the base fuel.

The present invention also provides a fuel composition for a spark-ignition internal combustion engine, said fuel composition comprising an additive composition according to the present invention and a base fuel.

Gasoline fuels (including those containing oxygenates) are typically used in spark-ignition internal combustion engines. Commensurately, the fuel composition that may be prepared according to the process of the present invention may be a gasoline fuel composition.

The fuel composition may comprise a major amount (i.e. greater than 50% by weight) of liquid fuel ("base fuel") and a minor amount (i.e. less than 50% by weight) of additive composition of the present invention. Examples of suitable liquid fuels include hydrocarbon fuels, oxygenate fuels and combinations thereof.

The fuel composition may contain octane-boosting fuel additive e in an amount of up to 20%, preferably from 0.1% to 10%, and more preferably from 0.2% to 5% weight additive/weight base fuel. Even more preferably, the fuel composition contains the fuel additive in an amount of from 0.25% to 2%, and even more preferably still from 0.3% to 1% weight additive/weight base fuel. It will be appreciated that, when more than one octane-boosting fuel additive e is used, these values refer to the total amount of fuel additive e in the fuel.

The fuel compositions may comprise at least one other further fuel additive. Examples of such other additives that may be present in the fuel compositions include detergents, friction modifiers/anti-wear additives, corrosion inhibitors, combustion modifiers, anti-oxidants, valve seat recession additives, dehazers/demulsifiers, dyes, markers, odorants, anti-static agents, anti-microbial agents, and lubricity improvers. Further octane improvers may also be used in the fuel composition, i.e. octane improvers which do not have the structure of octane-boosting fuel additive e.

The fuel compositions are used in a spark-ignition internal combustion engine. Examples of spark-ignition internal combustion engines include direct injection spark-ignition engines and port fuel injection spark-ignition engines. The spark-ignition internal combustion engine may be used in automotive applications, e.g. in a vehicle such as a passenger car.

The present invention also provides the use of BHT for stabilising a fuel additive e, as well as a method for stabilising a fuel additive e, said method comprising blending the fuel additive e with BHT.

The efficacy of BHT as a stabilising agent for the fuel additive e may be measured according to ASTM D1209-05 (2011).

The invention will now be described with reference to the following non-limiting examples.

EXAMPLES

HPLC analysis was carried out in the following examples using the conditions provided in the following table:

| Column: | Waters Symmetry Shield RP18, 150 × 4.6 mm, 3.5 μm | | |
|---|---|---|---|
| Mobile phase: | A: 0.1% (v/v) TFA in water B: 0.05% (v/v) TFA in 50:50 (v/v) acetonitrile/water | | |
| Gradient: | Time [min] | A [%] | B [%] |
| | 0 | 95 | 5 |
| | 15.0 | 95 | 5 |
| | 20.0 | 5 | 95 |
| | 20.1 | 5 | 95 |
| | 25.0 | 95 | 5 |
| Run time: | 25 min | | |
| Initial pump pressure: | 158 bar (QC023, col. 190) | | |
| Flow rate: | 1.0 mL/min | | |
| Column temperature: | 30° C. | | |
| Sample temperature: | Ambient | | |
| Detection: | Wavelength | 225 nm | |
| | Bandwidth | 4 nm | |
| | Peakwidth | >0.025 min (10 Hz) | |
| | Reference | Off | |
| Injection volume: | 10.0 μL | | |

The samples for use in HPLC analysis were prepared according to the following protocol:

| Step ia: | Extraction |
|---|---|
| | Obtain approximate reaction mixture concentration from lab. Weigh approximately 1 mL of reaction mixture and calculate the equivalent mass of chloroacetamide intermediate 3. Add ethyl acetate to afford a nominal concentration of 20 mg/mL chloroacetamide intermediate 3 plus 0.5 volume equivalents of water and a few drops of glacial acetic acid. Mix and allow to separate. |
| | Dilution |
| | Add 25 μL of the upper ethyl acetate layer to 5 mL dilution solvent B. |
| Step ib: | Extraction |
| | Obtain approximate reaction mixture concentration from lab. Weigh approximately 1 mL of reaction mixture and calculate the equivalent mass of benzoxazinone 4. Add ethyl acetate to afford a nominal concentration of 20 mg/mL benzoxazinone 4 plus 0.5 volume equivalents of water and a few drops of glacial acetic acid. Mix and allow to separate. |
| | Dilution |
| | Add 25 μL of the upper ethyl acetate layer to 5 mL dilution solvent B. |
| Step ii: | Extraction |
| | Obtain sample of OX-06 in toluene from lab. |
| | Dilution |
| | Add 50 μL of the toluene layer to 5 mL dilution solvent B and filter prior to analysis. |
| Method check: | If appropriate prepare a reference sample and chromatograph for retention time confirmation. For instance: Amino-methylphenol 1: Prepare samples to a nominal concentration of 0.2 mg/mL in dilution solvent A. |
| | Benzoxazinone 4: Prepare samples to a nominal concentration of 0.1 mg/mL in dilution solvent B. |
| | OX-06: Prepare samples to a nominal concentration of 0.2 mg/mL in dilution solvent B. |

Example 1: Industrial-Scale Preparation of an Octane-Boosting Fuel Additive e

An octane-boosting fuel additive e was prepared with high yield according to the following scheme:

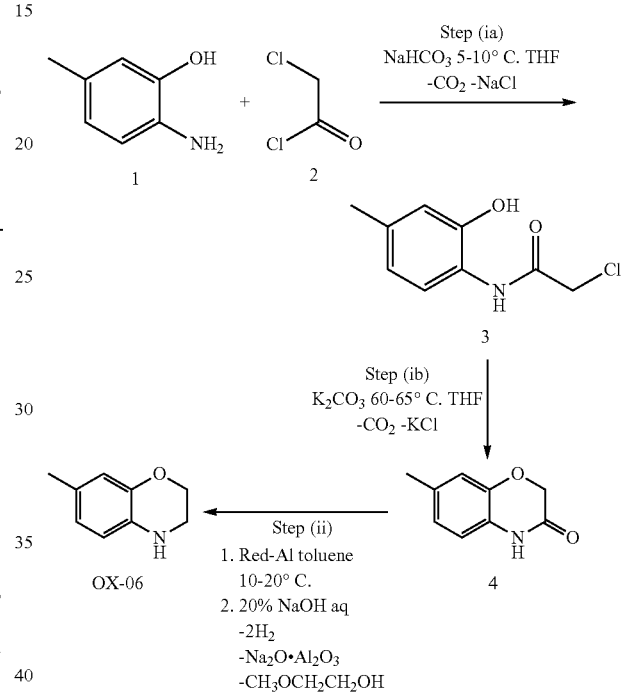

Materials

THF was used which contains BHT in an amount of approximately 300 ppm by weight.

Step (ia)

2-Amino-5-methylphenol 1 (100 kg, 812 mol) was charged to a 3000 L reactor (named here R103) followed by sodium bicarbonate (81.9 kg, 975 mol, 1.2 eq). Tetrahydrofuran (1067 kg, 12 eq vol) was charged and the suspension was stirred at 20° C. for 30 minutes then cooled to 5 to 10° C.

Chloroacetyl chloride 2 98% (98.6 kg, 873 mol, 1.075 eq) was added to the reactor over 6 hours at 10±2° C. During the addition an exotherm and off gassing ($CO_2$) was observed (cooling required to maintain desired temperature range). The reaction mixture was stirred at 10±2° C. for 1 hour.

The yellow-orange coloured suspension was sampled for analysis. HPLC showed complete conversion of 2-amino-5-methylphenol 1 to 2-chloro-N-(2-hydroxy-4-methylphenyl)acetamide) 3.

Step (ib)

In a separate 4500 L reactor (named here R105) a suspension of potassium carbonate powder (134.7 kg, 975 mol, 1.2 eq) and tetrahydrofuran (217 kg, 2.5 eq vol) were stirred at 20° C. The contents of reactor R103 were transferred to reactor R105 over 90 minutes maintaining the temperature at 20 to 25° C. The reactor R103 and the transfer lines were rinsed with THF (50 kg). The contents of reactor R105 were warmed to 60 to 65° C. over 4 hours.

After maintaining at 60 to 65° C. for 11 hours the suspension was sampled for analysis. HPLC showed 1.7% 2-chloro-N-(2-hydroxy-4-methylphenyl)acetamide 3 remaining. The reactor contents were heated at 65 to 66° C. for a further 4 hours and re-sampled. HPLC showed 99.9% conversion of 2-chloro-N-(2-hydroxy-4-methylphenyl)acetamide 3.

Demineralised water (1200 kg, 12 eq vol) was charged to reactor R105 over 90 minutes maintaining the temperature at 50 to 60° C. Tetrahydrofuran was then distilled out under reduced pressure, initially at 600 mbar and pulling in to 50 mbar at the end of the strip (maximum jacket temperature 60° C.), distillate weight 1450 kg. The resulting aqueous suspension of the product was cooled to 20 to 25° C., vented to nitrogen and stirred for 1 hour prior to filtration. The product was filtered off using a large Hastelloy pressure filter and blown down with nitrogen (filtrate weight 1228 kg). The light brown coloured solid was washed via the reactor with demineralised water (3×150 kg), blowing down each time (filtrate weight 440 kg).

The damp filter-cake (146 kg) was dried in the double cone vacuum drier at 50 to 60° C. under reduced pressure to constant weight (discharge spec≤0.1% by KF) to give 7-methyl-2H-benzo[b][1,4]oxazin-3(4H)-one 4 as a light brown solid. Recorded product weight was 127.9 kg, yield (based on $^1$H NMR assay)=93.9%. The HPLC purity was 99.0%, the $^1$H NMR assay was 97.3% w/w. The water content, measured by the Karl-Fisher (KF) analysis, was 0.04%.

The procedure was repeated on 98 kg 2-Amino-5-methylphenol 1 and yielded 126.7 kg 7-methyl-2H-benzo[b][1,4]oxazin-3(4H)-one 4.

Step (ii)

7-methyl-2H-benzo[b][1,4]oxazin-3(4H)-one 4 (127 kg, 778 mol, KF 0.04%) and toluene (1101 kg, 10 eq vol) were charged to a 2800 L reactor (named here R104) under nitrogen. The resulting suspension was stirred at 20° C. for 2 hours. A solution of sodium bis(2-methoxyethoxy)aluminium hydride 70% w/w in toluene (461 kg, 1596 mol, 2.05 eq) was added over 6.5 hours maintaining the temperature at 20±2° C. with cooling. The resulting clear red-orange solution was maintained at 20±2° C. for 24 hours then sampled for analysis. HPLC analysis showed 99.75% conversion, with 81.9% OX-06, 0.2% starter 4, 10.7% of a dimer by-product 5 and 7.2% total others.

The solution was cooled back to 5 to 10° C. prior to reaction quench with 20% NaOH solution (787 kg, 3935 mol). The quench is exothermic and hydrogen gas evolved (vented to atmosphere via a flame arrestor). The first 25 kg of the 20% NaOH solution was added over 4.25 hours maintaining the reactor temperature<15° C. The second charge of 20% NaOH (106 kg) was added over 2 hours at <20° C. The final 20% NaOH charge (656 kg) was added over 3 hours at <25° C. After the quench was complete the reactor contents were stirred for 2 hours at 20 to 25° C. then allowed to settle for 2 hours.

The lower aqueous phase (1008 kg) was removed and the organic phase (1390 kg) was collected. The aqueous layer was charged back to R104 followed by toluene (165 kg, 1.5 eq vol), the reactor contents were stirred for 30 minutes and allowed to separate (2 hours). The lower aqueous phase (956 kg) was removed and the original organic phase (1390 kg) was charged back to the reactor. The product toluene solution was washed with demineralised water (3×381 kg). Good separations were obtained, with the aqueous weight of 486 kg, 393 kg and 382 kg removed after the respective washes.

The toluene product solution (1490 kg) was stripped under reduced pressure in a 1360 L reactor (named here R106), using a jacket temp of 60° C. and pulling the vacuum in to 50 mbar at the end of the strip. The crude product was transferred to a drum and the reactor and lines were rinsed with toluene (20 kg). The concentrated crude product solution (145 kg, brown oil) was sampled for analysis. The yield based on the $^1$H NMR assay was 77.2% OX-06. The HPLC purity was 85.06% OX-06, 11.59% dimer 5, 0.18% BHT and 3.17% total others. The $^1$H NMR assay was 61.8% w/w.

The procedure was repeated on 115 kg 7-methyl-2H-benzo[b][1,4]oxazin-3(4H)-one 4 and yielded 158 kg concentrated crude product OX-06 solution, with a 85.3% yield based on the $^1$H NMR assay (56.8%).

Alternative methods for carrying out step (ii) were trialled on a laboratory-scale:

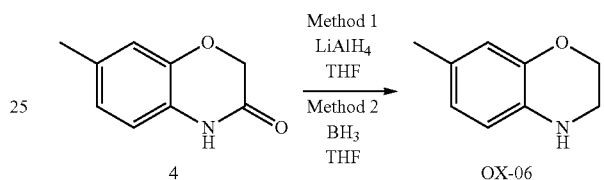

In a first method, lithium aluminium hydride pellets (76.65 g, 1.6 eq) were stirred under nitrogen in HPLC grade THF (2.5 L) then cooled to <10° C. Compound 4 (206 g) was added portion wise to the lithium aluminium hydride slurry, while maintaining the temperature<10° C. The reaction mixture was stirred at room temperature for 16 hours. The mixture was quenched with water, 15% aqueous NaOH was added and the slurry was stirred for 16 hours, filtered and extracted with EtOAc. The organic solvent was evaporated to a brown oil, which was distilled (120° C., 0.05 mmHg) to yield 175 g (93%) OX-06.

In a second method, compound 4 (10 g, 61 mmol) was suspended in dry THF (80 ml), the slurry was cooled to 0 to 5° C. and $BH_3$.THF (1.5 eq) was added. The reaction mixture was allowed to warm to ambient temperature, then heated to 60° C. for 16 hours, quenched with methanol and aqueous 1M HCl. The solvent was evaporated, the residue was basified with NaOH and extracted into diethyl ether. The ether phase was washed twice with water, dried over magnesium sulfate and the solvent was evaporated to give 9 g (99%) OX-06 as a yellow oil.

Example 2: Isolation of Octane-Boosting Fuel Additive e

The equipment used for distillation was an unstirred 400 L Hastelloy C22 still (named here R111). Glass overheads consisting of 1.5 metre×30 cm glass column packed with 1" glass Rashig rings (packed height 1.0 m) were used. The distillation head had an automatic reflux divider, a 9" condenser (held at 50° C.) and a high vacuum pump and hot oil circulator heater 12 kW.

The crude product solutions from Example 1 (batch 1: 145 kg and batch 2: 158 kg) were charged to R111 under vacuum (filtered via 5 micron filter), and the drums and lines were rinsed with toluene (20 kg). Initially the vacuum was set to 200 mbar and the oil heater set to 60° C., the temperature was then gradually increased and the pressure reduced to obtain a good reflux. The system was held under total reflux for 90 minutes before fraction collection (~20 L fractions taken).

Once the toluene had been stripped the temperature was increased and the vacuum pulled in to ~5 mbar. The system was held under total reflux for 90 minutes prior to product fraction collection. The distillation residue was removed by boiling out R111 with THF (200 L), the residue weight was ~30 kg. The resulted distillation mass balance was input 340.3 kg charged, output total distillates plus residue (333.3 kg) therefore mass balance=97.9%.

A summary of the conditions during the distillation process is provided in the following table:

| Fraction | Base temp (° C.) | Head temp (° C.) | Oil Set temp (° C.) | Vacuum (mbar) | Reflux ratio | Comments |
|---|---|---|---|---|---|---|
| 1-4 | 60-66 | 46-47 | 80 | 100 | 1:1 | colourless liquid (toluene fronts) |
| 5-9 | 66-117 | 47-20 | 100-120 | 100-40 | 1:1 | clear colourless (toluene fronts) |
| 10-11 | 137-139 | 135 | 150 | 5 | 10:1 | colourless distillate |
| 12-20 | 140-150 | 136-140 | 160-165 | 4-5 | 2:1 | colourless distillate |
| Residue | | | | | | Discharged as THF solution, estimated weight 30 kg. |

The fractions were analysed to determine inter alia the content of OX-06 and BHT. A summary of the analysis of the different fractions is provided in the following table:

| | | HPLC analysis | | GC analysis (% w/w) | |
|---|---|---|---|---|---|
| | Weight | 225 nm (A %) | | | 2-methoxy- |
| Fraction | (kg) | OX-06 | BHT | Other | Toluene | ethanol |
| 9 | 0.7 | — | — | — | 100 | <0.01 |
| 10 | 3.4 | 98.63 | 0.94 | 0.43 | 0.06 | <0.01 |
| 11 | 4.7 | 99.50 | 0.46 | 0.05 | <0.01 | <0.01 |
| 12 | 20.6 | 99.077 | 0.652 | 0.175 | <0.01 | <0.01 |
| 13 | 20.2 | 99.54 | 0.38 | 0.079 | <0.01 | <0.01 |
| 14 | 19.6 | 99.83 | 0.12 | 0.05 | <0.01 | <0.01 |
| 15 | 21.4 | 99.86 | 0.07 | 0.06 | <0.01 | <0.01 |
| 16 | 19.66 | 99.80 | 0.12 | 0.08 | <0.01 | <0.01 |
| 17 | 21.0 | 99.7 | <0.01 | 0.3 | <0.01 | <0.01 |
| 18 | 19.6 | 99.96 | <0.01 | 0.04 | <0.01 | <0.01 |
| 19 | 19.2 | 99.96 | <0.01 | 0.04 | <0.01 | <0.01 |
| 20 | 8.3 | 100 | <0.01 | <0.01 | <0.01 | <0.01 |

Fractions 10 to 20 were combined (176.1 kg) and analysed, providing OX-06 with the following specifications:
Appearance: clear colourless oil
HPLC purity at 225 nm: 99.76%, with 0.17% BHT, total others 0.07%.
Residual solvents (by GC): toluene<0.01%, 2-methoxyethanol<0.01%.
$^1$H NMR assay (300 MHz, DMSO solvent using 1,3,5-trimethylbenzene as standard): 99.3% w/w, with 0.13% w/w BHT.
Metals content (by atomic absorption spectrometry using a Perkin Elmer Analyst 300 Atomic Absorption Spectrometer, believed to give equivalent results to ASTM D7111-16): Al 11 ppm, K 0.15 ppm, Na none detected
Elemental analysis: Cl, 24 ppm, S, <5 ppm.

Example 3: Effect of BHT on OX-06 Stability

To determine the effect of trace BHT on the stability of OX-06, colour determination of BN-06 upon storage was made according to the Pt—Co/Hazen scale, using a method which gives equivalent results to ASTM D1209-05 (2011).

Samples of BN-06 containing different amounts of BHT were stored in the dark for periods of 0, 3, 7, 21 and 60 days. A Lovibond Nessleriser 2150 was employed for manual visualisation of the samples. 50 ml of liquid sample was introduced into glassware to give a sample path length of approximately 113 nm. Observations were made through the sample path length, and the sample compared to a colour-scaled filter. The graduated colour filters were checked using HPLC grade water (Millipore Direct-Q 3UV) and a platinum-cobalt 250 colour standard (VWR 84813.290). Quantification was limited up to 250 Hazen.

The results are provided in the following table:

| | Hazen (HPLC % area BHT) | | |
|---|---|---|---|
| | OX-06 Batch 1 fraction 1 | OX-06 Batch 1 fraction 2, no BHT | OX-06 Batch 2 |
| 0 | 150 (0.63) | 150 (0.0) | 150 (0.18) |
| 3 Days | 150 (0.72) | 200 (0.0) | 150 (0.17) |
| 7 Days | 175 (0.62) | >250 (0.0) | 200 (0.16) |
| 21 Days | 200 (0.60) | >250 (0.0) | >250 (0.16) |
| 60 Days | >>250 (0.12) | >>250 (0.0) | >>250 (0.48) |

For all samples, 150 Hazen was observed at start of testing and much greater than 250 Hazen was observed at the end of testing. However, those samples containing trace amounts of BHT exhibited a slower increase in Hazen than was observed in the samples that were free from BHT. Indeed, the stabilising effect of BHT was observed in samples containing BHT in an amount of as little as 0.18% by weight of fraction.

The dimensions and values disclosed herein are not to be understood as being strictly limited to the exact numerical values recited. Instead; unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A method for preparing a fuel additive having the formula:

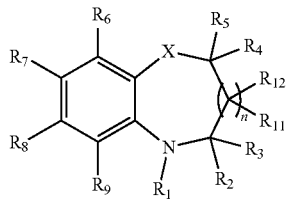

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1,
said method comprising carrying out the following reaction:

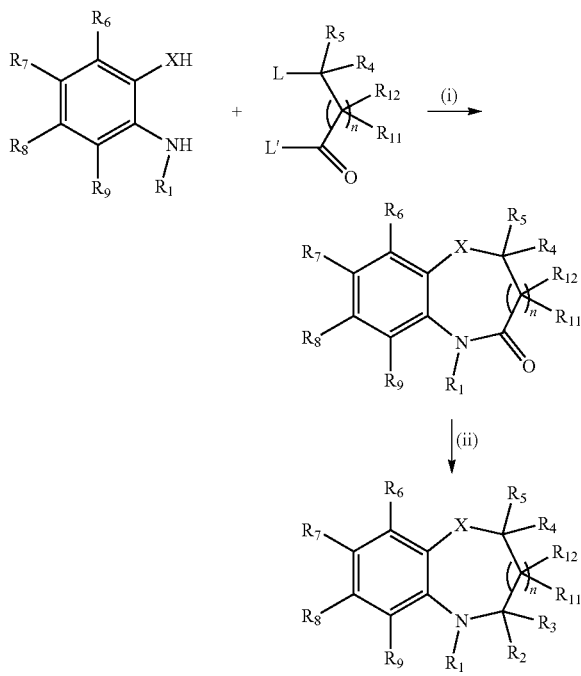

where: L and L' are each independently selected from leaving groups,
wherein step (i) is carried out in the presence of butylated hydroxytoluene.

2. A method according to claim 1, wherein step (i) comprises the following sub-steps:

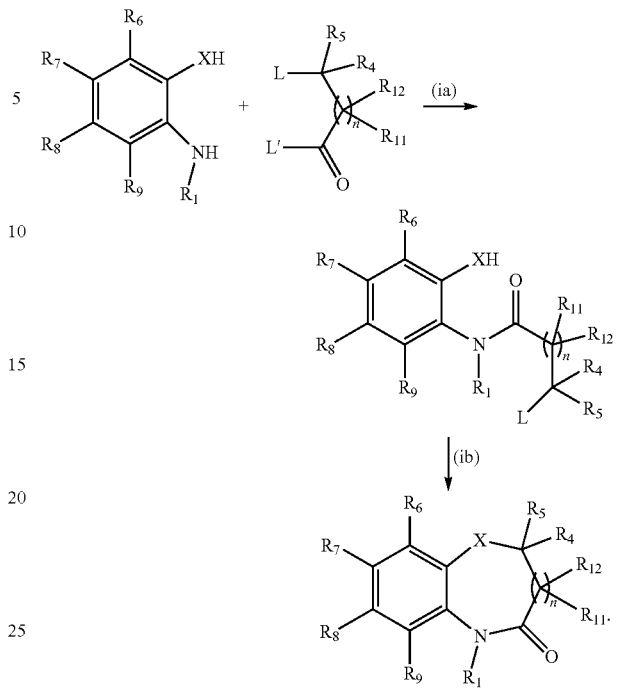

3. A method according to claim 2, wherein step (ia) is conducted in the presence of a base, and where the base is selected from inorganic bases.

4. A method according to claim 2, wherein step (ia) is conducted in the presence of an aprotic solvent.

5. A method according claim 2, wherein the method comprises cooling the reaction mixture during step (ia) to a temperature of up to 18° C.

6. A method according to claim 2, wherein step (ib) is conducted in the presence of a base, and where the base is selected from:
alkali metal carbonates; and
nitrogen-containing organic bases.

7. A method according to claim 2, wherein the method comprises heating the reaction mixture during step (ib) to a temperature of at least 40° C.

8. A method according to claim 1, wherein L is selected from: halides, substituted aryloxy groups and sulfonates.

9. A method according to claim 1, wherein step (ii) is carried out in the presence of a reducing agent or using catalytic reduction.

10. A method according to claim 9, wherein the reducing agent is selected from sodium bis(2-methoxyethoxy)aluminumhydride, lithium aluminium hydride, borane, diisobutylaluminium hydride, and borohydrides.

11. A method for preparing a fuel additive having the formula:

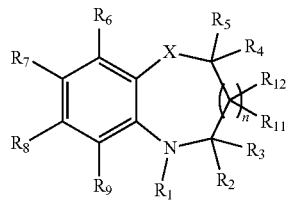

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —NR$_{10}$—, where $R_{10}$ is selected from hydrogen and alkyl groups; and
n is 0 or 1, said method comprising the following steps:
(1) preparing the fuel additive in the presence of butylated hydroxytoluene; and
(2) purifying the fuel additive by: (a) dissolving the fuel additive in a water-insoluble solvent to form a solution; (b) washing the solution with water; and (c) separating the fuel additive product from the water-insoluble solvent using distillation.

12. A method according to claim 1, wherein the butylated hydroxytoluene is introduced as part of the solvent system in which the reaction is conducted.

13. A method according to claim 1, wherein the method comprises preparing the fuel additive in a form which contains butylated hydroxytoluene in an amount of from 0.01 to 1.5% by weight of the fuel additive.

14. An additive composition for a fuel for a spark-ignition internal combustion engine, said additive composition comprising:
a fuel additive having the formula:

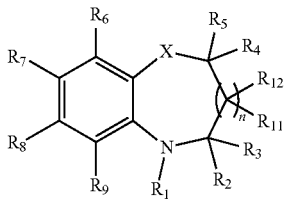

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —NR$_{10}$—, where $R_{10}$ is selected from hydrogen and alkyl groups; and
n is 0 or 1; and
butylated hydroxytoluene.

15. An additive composition according to claim 14, wherein butylated hydroxytoluene is present in an amount of from 0.01 to 1.5% by weight of the fuel additive.

16. An additive composition according to claim 14, wherein the additive composition is obtainable by a method comprising carrying out the following reaction:

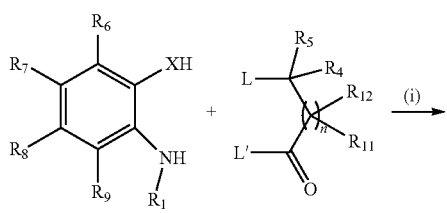

-continued

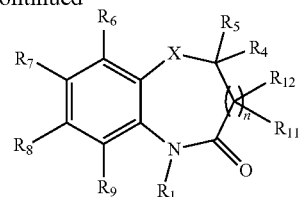

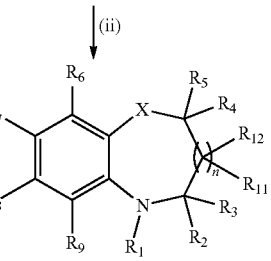

where: L and L' are each independently selected from leaving groups,
wherein step (i) is carried out in the presence of butylated hydroxytoluene.

17. A process for preparing a fuel composition for a spark-ignition internal combustion engine, said process comprising: blending an additive composition according to claim 14 with a base fuel.

18. A process according to claim 17, wherein the process comprises blending additional butylated hydroxytoluene with the fuel, preferably to give a total amount of butylated hydroxytoluene of up to 1000 ppm by weight of the base fuel.

19. A fuel composition for a spark-ignition internal combustion engine, said fuel composition comprising an additive composition according to claim 14 and a base fuel.

20. A method for stabilising a fuel additive having the formula:

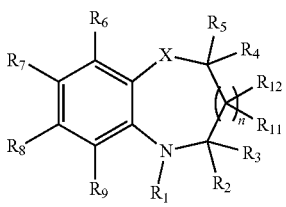

where: $R_1$, $R_2$ and $R_3$ are hydrogen;
$R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —NR$_{10}$—, where $R_{10}$ is selected from hydrogen and alkyl groups; and
n is 0 or 1,
said method comprising blending the fuel additive with butylated hydroxytoluene.

* * * * *